United States Patent [19]
Dyke et al.

[11] Patent Number: 6,069,151
[45] Date of Patent: May 30, 2000

[54] QUINOLINES AND THEIR THERAPEUTIC USE

[75] Inventors: Hazel Joan Dyke; John Gary Montana; Alan Findlay Haughan; Verity Margaret Sabin, all of Cambridge, United Kingdom

[73] Assignee: Darwin Discovery, Ltd., United Kingdom

[21] Appl. No.: 09/099,234

[22] Filed: Jun. 17, 1998

Related U.S. Application Data

[63] Continuation-in-part of application No. 08/965,554, Nov. 6, 1997, abandoned.

[30] Foreign Application Priority Data

| Nov. 6, 1996 | [GB] | United Kingdom | 9623163 |
| Jun. 17, 1997 | [GB] | United Kingdom | 9712761 |
| Jul. 7, 1997 | [GB] | United Kingdom | 9714298 |

[51] Int. Cl.$^7$ .............. A61K 31/4706; C07D 215/24; C07D 401/04; C07D 401/14
[52] U.S. Cl. .............. 514/314; 514/248; 514/249; 514/258; 514/301; 514/302; 514/303; 514/311; 544/235; 544/236; 544/264; 544/265; 544/350; 546/114; 546/116; 546/118; 546/167; 546/173
[58] Field of Search ................ 546/167, 173, 546/118, 116, 114; 544/235, 236, 264, 265, 350; 514/248, 258, 249, 314, 311; 574/301, 302, 303

[56] References Cited

U.S. PATENT DOCUMENTS

| 4,857,301 | 8/1989 | Czarniecki et al. .............. 424/40 |
| 4,910,193 | 3/1990 | Buchheit .............. 514/216 |
| 5,304,563 | 4/1994 | Raddatz et al. .............. 514/311 |
| 5,340,811 | 8/1994 | Kajihara et al. .............. 514/253 |
| 5,545,647 | 8/1996 | Tanaka .............. 514/343 |

FOREIGN PATENT DOCUMENTS

| 0498722 | 2/1992 | European Pat. Off. . |
| 0545170 | 6/1993 | European Pat. Off. . |
| 0582908 | 2/1994 | European Pat. Off. . |
| 2184673 | 1/1989 | Japan . |
| 9307146 | 10/1992 | WIPO . |
| 9422852 | 3/1994 | WIPO . |
| 9412461 | 6/1994 | WIPO . |
| 9636595 | 5/1996 | WIPO . |
| 9636596 | 5/1996 | WIPO . |
| 9636611 | 5/1996 | WIPO . |

OTHER PUBLICATIONS

Ashaks J. et al. Chem. Pap. 39(5), 667–86, 1985.
Nicholson CD et al. TIPS. 12, 19–27, Jan. 1991.
Merchant JR et al. J. Indian Chem. Soc. 48(5), 427–31, 1971.
Chakravorti SS. et al. Indian J. Chem. 5(1), 24–6, 1967.

Trecourt, F. et al. (1995) "Synthesis of 7H–Pyrido [2,3–c] carbazoles from 5–Bromo–8–methoxyquinolines via Coupling and Azide Cyclization Reactions" J. Heterocyclic Chem. 32:1261–1267.

Trecourt, F. et al. (1995) "Substitued 8–Methoxyquinolines: Regioselective Bromination, Coupling Reactions, and Cyclization to an 11H–Indolo[3,2–c] Quinoline" Syn. Commum. 25:4011–4024.

Khalil, Z.H. et al. (1990) "Synthesis and microbial activity of 5–heterocyclo–8–hydroxyquinolines" J. Indian Chem. Soc. 67(10):821–823.

Beugelmans, R., M. Bois–Choussy (1991) "$S_{RN}1$–Based Methodlgy for Synthesis of Naphthylquinolines and Naphthylisoquinolines" J. Org. Chem 56:2518–2522.

Gopalchari, R., M.L. Dhar (1960) "Potential amebicides. IX. Synthesis of 5,5'–bis(8–hydroxyquinaldine) and some of their tetrahydo, iodo, allyl, and Mannich derivatives" J. Sci. Ind. Res. 19C:233–237 (abstract only).

Ghosh, T.N. et al. (1963) "Quinoline derivatives. XVII. Potential amebicidal agents" Indian J. Chem. 1:168–171 (abstract only).

Khalil, Z.H. et al. (1987) Synthesis of some Oxazolo–, Imidazolo–, Selenadiazolo–, Thiadiazolo–,Azetidinono–, and Thiazolidinonoo–8–Hydroxyquinolines. J. Indian Chem. Soc. 64: 42–45.

Nicholoson, C.D. et al. (1991) Differential modulation of tissue function and therapeutic potential of selective inhibitors of cyclic nucleotide phosphodiesterase isoenzymes. TIPS 12: 19–27.

Primary Examiner—Evelyn Mei Huang
Attorney, Agent, or Firm—Saliwanchik, Lloyd & Saliwanchik

[57] ABSTRACT

Compounds of the formula

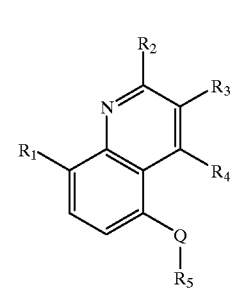

(i)

have therapeutic utility, as inhibitors of phosphodiesterase IV and TNF release.

21 Claims, No Drawings

QUINOLINES AND THEIR THERAPEUTIC USE

REFERENCE TO RELATED APPLICATION

This application is a continuation-in-part of application Ser. No. 08/965,554, filed Nov. 6, 1997, abandoned.

FIELD OF THE INVENTION

The present invention relates to novel quinolines, and to their formulation and use as pharmaceuticals.

BACKGROUND OF THE INVENTION

Japanese Patent Publication 2-184673 discloses quinolinesulphonamides.

U.S. Pat. No. 4,910,193 discloses quinolinesulphonamides, in which the sulphonamide nitrogen is substituted by a variety of bridged saturated ring systems, as medicaments suitable for the treatment of serotonin-induced gastrointestinal disturbances.

U.S. Pat. Nos. 4,857,301 and 5,340,811 disclose quinolinesulphonamides in the treatment of asthma, respectively as bronchodilators and as anti-allergic compounds.

Trecourt et al., J. Het. Chem (1995) 32 1261, describe the preparation of 5-arylquinolines as intermediates for the synthesis of pyridocarbazoles. Trecourt et al., *Syn. Commun.* (1995) 25 4011, describe 5-phenylquinolines as intermediates for the synthesis of indoloquinolines.

5-Heteroarylquinolines and 5-heterocycloquinolines with anti-microbial activity are described by Khalil et al., J. Indian Chem. Soc. (1987) LXIV 42, and ibid (1990) 67 821.

A series of patents by Bayer (including U.S. Pat. No. 5,304,563, EP-A-0582908 and EP-A-0545170) discloses 2-substituted quinolines, including 5-arylquinolines, as lipoxygenase inhibitors.

WO-A-9412461 discloses catechol diethers as selective phosphodiesterase inhibitors. Phosphodiesterases (PDE) and Tumour Necrosis Factor (TNF), their modes of action and the therapeutic utilities of inhibitors thereof, are described in WO-A-9636595, WO-A-9636596 and WO-A-9636611, the contents of which are incorporated herein by reference. The same documents disclose sulphonamides having utility as PDE and TNF inhibitors.

Certain quinolines are known, without associated therapeutic activity. These include 5,5'-bis(8-methoxyquinoline), 5,5'-bis(8-methoxyquinoline), 1-(8-ethoxy-5-quinolyl)-3,4-dihydroisoquinoline, 1-(8-ethoxy-5-quinolyl)isoquinoline, 2-(8-ethoxy-5-quinolyl)-1,2,3,4-tetrahydroisoquinoline, 8-isopropoxy-5-(1-naphthyl)quinoline, 5-methoxy-8-phenylquinoline, 5-methoxy-8-[2-(t-butylcarbonylamino) phenyl]quinoline and 5-methoxy-8-[2-(t-butylcarbonylamino)-5-methoxyphenyl]quinoline. See Chem. Abs. (1962) 57(9):11159e; Chem. Abs. (1963) 59(6) :6364e; Beugelmans & Bois-Chaussy, J. Org. Chem. (1991) 56:2518–2522; and Trécourt et al, J. Heterocyclic Chem. (1995) 32:1261.

SUMMARY OF THE INVENTION

This invention is based on the discovery of novel compounds that can be used to treat disease states, for example disease states associated with proteins that mediate cellular activity, for example by inhibiting tumour necrosis factor and/or by inhibiting phosphodiesterase IV. According to the invention, the novel compounds are of formula (i):

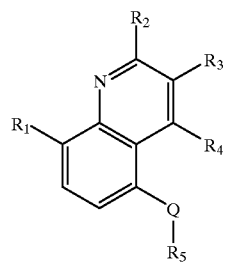

$R_1$ represents $C_{1-6}$ alkoxy (alkyl portion optionally substituted with one or more halogens), OH or thioalkyl;

$R_2$, $R_3$ and $R^4$, which may be the same or different, represent H, $OR_{11}$, $COR_7$, CN, $CO_2R_8$, $C(=NOR_7)R_7$, alkyl-$C(=NOR_7)R_7$, halogen, $CF_3$, $CONR_{12}R_{13}$, $NR_9R_{10}$ or $R_7$;

$R_5$ represents H or a substituents selected from halogen, arylalkyl, heteroarylalkyl, heterocycloalkyl, alkyl, hydroxy, alkoxy, $CO_2R_{11}$, $SO_2NR_{12}R_{13}$, $CONR_{12}R_{13}$, CN, $NR_9R_{10}$, $COR_{11}$ and $S(O)_{11}R_{11}$;

$R_7$ represents H, alkyl, cycloalkyl, aryl, heteroaryl, heterocyclo, arylalkyl, heteroarylalkyl or heterocycloalkyl, any of which may be optionally substituted at any position with $R^{16}$;

$R_8$ represents H, alkyl, arylalkyl, heteroarylalkyl or heterocycloalkyl;

$R^9$ represents alkylcarbonyl, alkoxycarbonyl, arylsulphonyl, heteroarylsulphonyl, heterocyclosulphonyl, arylcarbonyl, heteroarylcarbonyl, heterocyclocarbonyl or alkylsulphonyl and $R_{10}$ represents H or $R_{11}$, or $NR_9R_{10}$ represents a heterocyclic ring (such as morpholine or piperidine) optionally substituted with one or more $R_{15}$;

$R_{11}$ represents alkyl, cycloalkyl, aryl, heteroaryl, heterocyclo, arylalkyl, heteroarylalkyl or heterocycloalkyl;

$R_{12}$ and $R_{13}$, which may be the same or different, each represent $R_7$, or $NR_{12}R_{13}$ represents a hetercyclic ring (such as morpholine or piperidine) optionally substituted with one or more $R_{15}$;

$R_{15}$ represents alkyl, arylalkyl or heteroalkyl;

$R_{16}$ represents halogen, hydroxy, $OR_{11}$, $NR_9R_{10}$, CN, $CO_2H$, $CO_2R_{11}$, $CONR_{12}R_{13}$ or $COR_{11}$;

n represents 0–2; and

Q represents an aryl or heteroaryl ring, attached through any appropriate atom and optionally substituted at any position(s) with one or more substituents $R_5$; and pharmaceutically-acceptable salts thereof.

DESCRIPTION OF THE INVENTION

One aspect of this invention comprises compounds of the formula

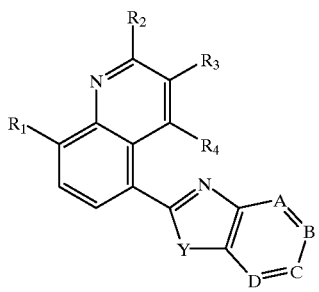

(i)

wherein A, B, C and D are the same or different and are each N, NO or $CR_{17}$, provided that not more than two are N or NO;

Y represents $NR_{18}$, O or S;

$R_{17}$ represents H, halogen, alkyl, $CF_3$, hydroxy, $OR_{10}$, $COR_{11}$, $SO_2R_{11}$, $SO_2NR_{12}R_{13}$, $NR_9R_{10}$, CN, $CO_2R_{10}$, $CONR_{12}R_{13}$, $NHSO_2CF_3$ or tetrazolyl, or is $R_5$ as defined above; and $R_{18}$ represents H or $C_{1-6}$ alkyl.

Suitable pharmaceutically-acceptable salts are pharmaceutically-acceptable base salts and pharmaceutically-acceptable acid addition salts. Certain of the compounds of formula (i) which contain an acidic group form base salts. Suitable pharmaceutically-acceptable base salts include metal salts, such as alkali metal salts for example sodium salts, or organic amine salts such as that provided with ethylenediamine.

Certain of the compounds of formula (i) which contain an amino group form acid addition salts. Suitable acid addition salts include pharmaceutically-acceptable inorganic salts such as the sulphate, nitrate, phosphate, borate, hydrochloride and hydrobromide and pharmaceutically-acceptable organic acid addition salts such as acetate, tartrate, maleate, citrate, succinate, benzoate, ascorbate, methanesulphate, α-ketoglutarate, α-glycerophosphate and glucose-1-phosphate. The pharmaceutically-acceptable salts of the compounds of formula (i) are prepared using conventional procedures.

It will be appreciated by those skilled in the art that some of the compounds of formula (i) may exist in more than one tautomeric form. This invention extends to all tautomeric forms.

It will be appreciated that the compounds according to the invention can contain one or more asymmetrically substituted atoms. The presence of one or more of these asymmetric centers in a compound of formula (i) can give rise to stereoisomers, and in each case the invention is to be understood to extend to all such stereoisomers, including enantiomers and diastereoisomers, and mixtures including racemic mixtures thereof.

When used herein the term alkyl whether used alone or when used as a part of another group includes straight and branched chain alkyl groups containing up to 6 atoms. Alkoxy means an alkyl-O- group in which the alkyl group is as previously described. Aryloxy means an aryl-O- group in which the aryl group is as defined below. Heteroaryloxy means a heteroaryl-O-group and heterocylooxy means a heterocyclo-O-group in which the heteroaryl and heterocyclo group are as defined below. Alkylamino means an alkyl-N- group in which the alkyl group is as previously defined, arylamino means aryl-N- and heteroarylamino means an heteroaryl-N- group (aryl and heteroaryl defined below). Cycloalkyl includes a non-aromatic cyclic or multicyclic ring system of about 3 to 10 carbon atoms. The cyclic alkyl may optionally be partially unsaturated. Aryl indicates carbocyclic radicals containing about 6 to 10 carbon atoms. Arylalkyl means an aryl-alkyl-group wherein the aryl and alkyl are as described herein. Heteroarylalkyl means a heteroaryl-alkyl group and heterocycloalkyl means a heterocyclo-alkyl group. Alkylcarbonyl means an alkyl-CO- group in which the alkyl group is as previously described. Arylcarbonyl means an aryl-CO-group in which the aryl group is as previously described. Heteroarylcarbonyl means a heteroaryl-CO- group and heterocyclocarbonyl means a heterocyclo-CO- group. Arylsulphonyl means an aryl-$SO_2$-group in which the aryl group is as previously described. Heteroarylsulphonyl means a heteroaryl-$SO_2$-group and heterocyclosulphonyl means a heterocyclo-$SO_2$-group. Alkoxycarbonyl means an alkyloxy-CO- group in which the alkoxy group is as previously described. Carbonyl oxygen means an alkyl-$SO_2$- group in which the alkyl group is as previously described. Alkylsulphonyl means an alkyl-$SO_2$- group in which the alkyl group is as previously described. Carbonyl oxygen means a —CO-group. It will be appreciated that a carbonyl oxygen cannot be a substituent on an aryl or heteroaryl ring. Heterocyclic ring means about a 5 to about a 10 membered monocyclic or multicyclic ring system (which may be saturated or partially unsaturated) wherein one or more of the atoms in the ring system is an element other than carbon chosen from amongst nitrogen, oxygen or sulphur atoms. Examples include morpholine and piperidine. Heteroaryl means about a 5 to about a 10 membered aromatic monocyclic or multicyclic hydrocarbon ring system in which one or more of the atoms in the ring system is an element other than carbon, chosen from amongst nitrogen, oxygen or sulphur, if desired, a N atom may be in the form of an N-oxide. Heterocyclo means about a 5 to about a 10 membered saturated or partially saturated monocyclic or multicyclic hydrocarbon ring system in which one or more of the atoms in the ring system is an element other than carbon, chosen from amongst nitrogen, oxygen or sulphur. Halogen means fluorine, chlorine, or bromine or iodine.

Compounds of the invention are useful for the treatment of TNF mediated disease states. "TNF mediated disease or disease states" means any and all disease states in which TNF plays a role, either by production of TNF itself, or by TNF causing another cytokine to be released, such as but not limited to IL-1 or IL-6. A disease state in which IL-1, for instance, is a major component, and whose production or action is exacerbated or secreted in response to TNF, would therefore be considered a disease state mediated by TNF. As TNF-β (also known as lymphotoxin) has close structural homology with TNF-α (also known as cachectin), and since each induces similar biologic responses and binds to the same cellular receptor, both TNF-α and TNF-β are considered to be inhibited by compounds of the present invention and thus are herein referred to collectively as "TNF" unless specifically indicated otherwise.

This invention relates to a method for mediating or inhibiting the enzymatic activity or catalytic activity of PDE IV in a mammal in need thereof and for inhibiting the production of TNF in a mammal in need thereof, which comprises administering to said mammal an effective amount of a compound of Formula (i) or a pharmaceutically-acceptable salt thereof.

PDC IV inhibitors are useful in the treatment of a variety of allergic and inflammatory diseases, including: asthma, chronic bronchitis, chronic obstructive airways disease, atopic dermatitis, atopic eczema, urticaria, allergic rhinitis, allergic conjuctivitis, vernal conjunctivitis, inflammation of the eye, allergic responses in the eye, eosinophilic granuloma, psoriasis, Bechet's disease, erythematosis, anaphylactoid purpura nephritis, joint inflammation, arthritis, rheumatoid arthritis and other arthritic conditions such as rheumatoid spondylitis and osteoarthritis, septic shock, sepsis, ulcerative colitis, Crohn's disease, reperfusion injury of the myocardium and brain, chronic glomerulonephritis, endotoxic shock and adult respiratory distress syndrome. In addition, PDE IV inhibitors are useful in the treatment of diabetes insipidus and conditions associated with cerebral metabolic inhibition, such as cerebral senility, senile dementia (Alzheimer's disease), memory impairment associated with Parkinson's disease, depression and multi-infarct dementia. PDE IV inhibitors are also useful in conditions ameliorated by neuroprotectant activity, such as cardiac arrest, stroke and intermittent claudication. PDE IV inhibitors may be useful in the treatment of tardive dyskinesia, ischaemia and Huntingdon's disease. Additionally, PDE IV inhibitors could have utility as gastroprotectants. A special embodiment of the therapeutic methods of the present invention is the treatment of asthma.

The viruses contemplated for treatment herein are those that produce TNF as a result of infection, or those which are sensitive to inhibition, such as by decreased replication, directly or indirectly, by the TNF inhibitors of Formula (i). Such viruses include, but are not limited to HIV-1, HIV-2 and HIV-3, cytomegalovirus (CMV), influenza, adenovirus and the Herpes group of viruses, such as, but not limited to, *Herpes zoster* and *Herpes simplex*.

This invention more specifically relates to a method of treating a mammal, afflicted with a human immunodeficiency virus (HIV), which comprises administering to such mammal an effective TNF inhibiting amount of a compound of Formula (i) or a pharmaceutically-acceptable salt thereof.

The compounds of this invention may also be used in association with the veterinary treatment of animals, other than humans, in need of inhibition of TNF production. TNF mediated diseases for treatment, therapeutically or prophylactically, in animals include disease states such as those noted above, but in particular viral infections. Examples of such viruses include, but are not limited to feline immunodeficiency virus (FIV) or other retroviral infection such as equine infectious anemia virus, caprine arthritis virus, visna virus, maedi virus and other lengiviruses.

The compounds of this invention are also useful in treating parasite, yeast and fungal infections, where such yeast and fungi are sensitive to upregulation by TNF or will elicit TNF production in vivo. A preferred disease state for treatment is fungal meningitis.

Compounds of the invention may also suppress neurogenic inflammation through elevation of cAMP in sensory neurones. They are, therefore, analgesic, anti-tussive and anti-hyperalgesic in inflammatory diseases associated with irritation and pain.

The compounds of formula (i) are preferably in pharmaceutically-acceptable form. By pharmaceutically-acceptable form is meant, inter alia, of a pharmaceutically-acceptable level of purity excluding normal pharmaceutical additives such as diluents and carriers, and including no material considered toxic at normal dosage levels. A pharmaceutically-acceptable level of purity will generally be at least 50% excluding normal pharmaceutical additives, preferably 75%, more preferably 90% and still more preferably 95%.

The invention further provides a process for the preparation of a compound of formula (i), in which $R_1$ etc. are as defined above. It will be appreciated that functional groups such as amino, hydroxyl or carboxyl groups present in the various compounds described below, and which it is desired to retain, may need to be in protected forms before any reaction is initiated. In such instances, removal of the protecting group may be the final step in a particular reaction sequence. Suitable protecting groups for such functionality will be apparent to those skilled in the art. For specific details, see Protective Groups in Organic Synthesis, Wiley Interscience, T. W. Greene. Thus the process for preparing compounds of formula (i) in which $R_3$ contains an —OH group comprises deprotecting (for example by hydrogenolysis or hydrolysis) a compound of formula (i) in which $R_3$ contains an appropriate —OP wherein P represents a suitable protecting group (e.g. benzyl or acetyl).

It will be appreciated that where a particular stereoisomer of formula (i) is required, this may be obtained by conventional resolution techniques such as high performance liquid chromatography or the synthetic processes herein described may by performed using the appropriate homochiral starting material.

Compounds of the invention may be prepared by generally known processes from starting materials that are known or can readily be prepared by methods known to those of ordinary skill in the art. For example, procedures described in WO-A-9412461 and Biorganic & Med. Chem. Letters (1995) 5(17):1969, may be used, substituting for the catechol nucleus an appropriately substituted quinoline. The quinoline nucleus may be prepared as described in PCT/GB97/01359-60. Reference may also be made to the procedures given in J. Indian Chem. Soc. LXIV:42–45 (1987), and in the Examples below. Appropriate modifications will be evident to those of ordinary skill in the art.

A process for the preparation of a compound of formula (i) comprises reaction of a bromide of formula (ii) with a suitably substituted aryl or heteroaryl portion, for example an aryl or heteroarylboronic acid of formula (iii)

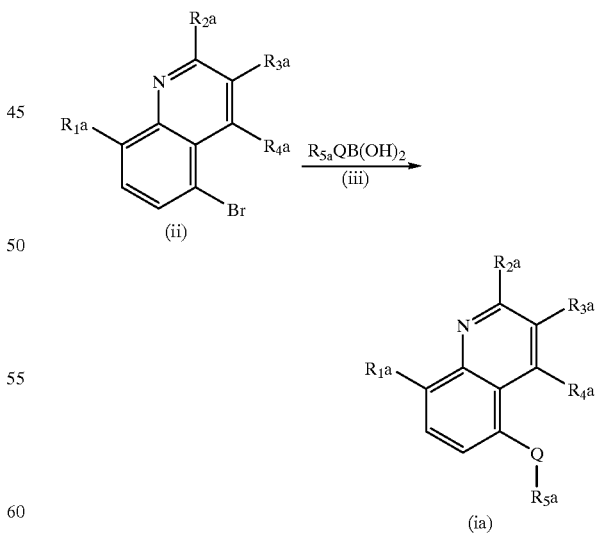

wherein $R_{12}$ represents $R_1$ as defined in relation to formula (i) or a group convertable to $R_1$ and $R_{2a}$–$R_{3a}$ similarly represent $R_2$–$R_5$ or groups convertible to $R_2$–$R_5$ respectively; and thereafter, if required, converting any group $R_{1a}$ to $R_1$ and/or $R_{2a}$ to $R_2$ and/or $R_{3a}$ to $R_3$ and/or $R_{4a}$ to $R_4$ and/or converting any group $R_{5a}$ to $R_5$. Alternatively, a bromide of formula (ii) may be converted into the corresponding boronic acid (using standard conditions known to those skilled in the art) and this may be coupled with an aryl or heteroaryl halide, preferably a bromide.

This coupling reaction may be carried out under any standard conditions known to those skilled in the art, for example conditions described by Trecourt et al, *J. Het. Chem.* (1995) 32 1261, and references cited therein. The preparation of bromides of formula (ii) is described in WO-A-9744036. Boronic acids of formula (iii) are commercially available, previously described compounds, or are prepared using standard conditions known to those skilled in the art.

A compound of formula (i) may also be prepared by interconversion of other compounds of formula (i). For example, a compound in which $R_5$ contains a carboxylic acid may be prepared by appropriate hydrolysis of a compound in which $R_5$ contains an alkoxycarbonyl group (for example a methoxycarbonyl group).

Compounds in which $R_2$–$R_4$ contain a CO group, e.g. CO-alkyl, CO-aryl, CO-heteroaryl, CO-alkylaryl, CO-alkylheteroaryl or CO-alkylheterocyclo, may be prepared from compounds in which $R_2$–$R_4$ contain a CN group, by addition of a suitable organometallic agent (such as a Grignard reagent).

By way of further example, compounds in which $R_2$–$R_4$ contain an oxime may be prepared from compounds in which $R_2$–$R_4$ contain a carbonyl group. This transformation may be carried out using any appropriate standard conditions known to those skilled in the art. Compounds of formula (i) in which $R_2$–$R_4$ contain a carbonyl group may be reduced using standard conditions known to those skilled in the art (for example with sodium borohydride in an appropriate solvent) to provide compounds in which $R_2$–$R_4$ contains an alcohol group. Compounds in which $R_2$–$R_4$ is alkyl may be prepared by reduction of compounds in which $R_2$–$R_4$ is CO-alkyl using standard conditions known to those skilled in the art (for example hydrazine hydrate in the presence of a suitable base in an appropriate solvent). Other transformations may be carried out on compounds of formula (i) in which $R_2$–$R_4$ contains a carbonyl group. Such transformations include, but are not limited to, reductive amination and alkylation. Any of the above transformations may be carried out either at the end of the synthesis or on an appropriate intermediate.

A compound of formula (i) or where appropriate a pharmaceutically-acceptable salt thereof and/or a pharmaceutically-acceptable solvate thereof, may be administered per se or, preferably, as a pharmaceutical composition also comprising a pharmaceutically-acceptable carrier.

Accordingly, the present invention provides a pharmaceutical composition comprising a compound of formula (i) or where appropriate a pharmaceutically-acceptable salt thereof and/or a pharmaceutically-acceptable solvate thereof, and a pharmaceutically-acceptable carrier.

The active compound may be formulated for administration by any suitable route, the preferred route depending upon the disorder for which treatment is required, and is preferably in unit dosage form or in a form that a human patient may administer to himself in a single dosage. Advantageously, the composition is suitable for oral, rectal, topical, parenteral administration or through the respiratory tract. Preparations may be designed to give slow release of the active ingredient.

The term parenteral as used herein includes subcutaneous injection, intravenous intramuscular, intrasternal injection or infusion techniques. In addition to the treatment of warm-blooded animals such as mice, rats, horses, cattle, sheep, dogs, cats, etc, the compounds of the invention are effective in the treatment of humans.

The compositions of the invention may be in the form of tablets, capsules, sachets, vials, powders, granules, lozenges, suppositories, reconstitutable powders, or liquid preparation such as oral or sterile parenteral solutions or suspensions. Topical formulations are also envisaged where appropriate.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers for example microcrystalline cellulose, lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically-acceptable wetting agents such as sodium lauryl sulphate.

The solid oral compositions may be prepared by conventional methods of blending, filling, tableting or the like. Repeated blending operations may be used to distribute the active agent throughout those compositions employing large quantities of fillers.

Such operations are of course conventional in the art. The tablets may be coated according to methods well known in normal pharmaceutical practice, in particular with an enteric coating.

Oral liquid preparations may be in the form of, for example, emulsions, syrups or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example, lecithin, sorbitan monooleate, or acacia, non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

Compositions may also suitably be presented for administration to the respiratory tract as a snuff or an aerosol or solution for a nebuliser, or as a microfine powder for insufflation, alone or in combination with an inert carrier such as lactose. In such a case the particles of active compound suitably have diameters of less than 50 $\mu$m, such as from 0.1 to 50 $\mu$m, preferably less than 10 $\mu$m, for example from 1 to 10 $\mu$m, 1 to 5 $\mu$m or from 2 to 5 $\mu$m. Where appropriate, small amounts of other anti-asthmatics and bronchodilators for example sympathomimetic amines such as isoprenaline, isoetharine, salbutamol, phenylephrine and ephedrine; corticosteroids such as prednisolone and adrenal stimulants such as ACTH may be included.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilised before filling into a suitable vial or ampoule and sealing.

Advantageously, adjuvants such as local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

Compounds of formula (i), or if appropriate a pharmaceutically-acceptable salt thereof and/or a pharmaceutically-acceptable solvate thereof, may also be administered as a topical formulation in combination with conventional topical excipients.

Topical formulations may be presented as, for instance, ointments, creams or lotions, impregnated dressings, gels, gel sticks, spray and aerosols, and may contain appropriate conventional additives such as preservatives, solvents to assist drug penetration and emollients in ointments and creams. The formulations may contain compatible conventional carriers, such as cream or ointment bases and ethanol or oleyl alcohol for lotions.

Suitable cream, lotion, gel, stick, ointment, spray or aerosol formulations that may be used for compounds of formula (i) or if appropriate a pharmaceutically-acceptable salt thereof, are conventional formulations well known in the art, for example, as described in standard text books such as Harry's Cosmeticology published by Leonard Hill Books, Remington's Pharmaceutical Sciences, and the British and U.S. Pharmacopoeias.

Suitably, the compound of formula (i), or if appropriate a pharmaceutically-acceptable salt thereof, will comprise from about 0.5 to 20% by weight of the formulation, favourably from about 1 to 10%, for example 2 to 5%.

The dose of the compound used in the treatment of the invention will vary in the usual way with the seriousness of the disorders, the weight of the sufferer, and the relative efficacy of the compound. However, as a general guide suitable unit doses may be 0.1 to 1000 mg, such as 0.5 to 200, 0.5 to 100 or 0.5 to 10 mg, for example 0.5, 1, 2, 3, 4 or 5 mg; and such unit doses may be administered more than once a day, for example 2, 3, 4, 5 or 6 times a day, but preferably 1 or 2 times per day, so that the total daily dosage for a 70 kg adult is in the range of about 0.1 to 1000 mg, that is in the range of about 0.001 to 20 mg/kg/day, such as 0.007 to 3, 0.007 to 1.4, 0.007 to 0.14 or 0.01 to 0.5 mg/kg/day, for example 0.01, 0.02, 0.04, 0.05, 0.06, 0.08, 0.1 or 0.2 mg/kg/day, and such therapy may extend for a number of weeks or months.

When used herein the term "pharmaceutically-acceptable" encompasses materials suitable for both human and veterinary use.

The following Examples illustrate the invention.

Intermediate 1
8-Methoxyquinoline-5-carboxylic acid chloride, hydrochloride

A suspension of 8-methoxyquinoline-5-carboxylic acid (5.0 g) in dichloromethane (50 ml) was cooled to 20 C. Oxalyl chloride (4.29 ml) was added cautiously and then dry dimethylformamide (8 drops) was added dropwise. The mixture was stirred at 0° C. for 1h and then at room temperature for 24h. The solvent was removed in vacuo and the residue azeotroped with a small amount of toluene. The title compound was obtained as a brown solid (5.18 g).
NMR (200 MHz, $d_6$-DMSO) δ 9.96(d, 1H), 9.18(dd, 1H), 8.52(d, 1H), 8.12(dd, 1H), 7.61(d, 1H), 4.20(s, 3H).

Intermediate 2
8-Methoxyquinoline-5-[N-(2-amino-5-carbomethoxyphenyl)]carboxamide A solution of methyl 3,4-diaminobenzoate (1.27 g) in dry pyridine (10 mg) was cooled to 0° C. under nitrogen. A suspension of 8-methoxyquinoline-5-carbonyl chloride, hydrochloride (1.97 g) in dry tetrahydrofuran was added, the resultant suspension was allowed to warm to room temperature and then stirred for 16h. The resultant suspension was heated at 60° C. for 16h and then cooled to room temperature. The mixture was concentrated in vacuo and ethyl acetate (100 ml) and 2M hydrochloric acid (50 ml) were added. The resultant precipitate was collected by filtration to provide the title compound as a brown solid (919 mg).
TLC $R_f$ 0.52 (10% methanol in dichloromethane).

Intermediate 3
8-Methoxy-2-trifluoromethylquinoline-5-[N-(2-amino-5-carbomethoxyphenyl)]carboxamide A solution of methyl 3,4-diaminobenzoate (1.0 g) in dry pyridine (25 ml) and triethylamine (1.7 ml) was cooled to 0° C. under nitrogen. A suspension of 8-methoxy-2-trifluoromethylquinoline-5-carbonyl chloride, hydrochloride (1.8 g; Intermediate 35 of PCT/GB97/01359) in dry tetrahydrofuran (40 ml) was added; the resultant suspension was allowed to warm to room temperature and then stirred overnight. The solvent was removed in vacuo and the residue partitioned between ethyl acetate (200 ml) and water (200 ml). The solid precipitate was removed by filtration and dried in vacuo at 45° C. to yield the title compound as an off white solid (1.34 g).
Mass spectrum (E1) 420 $[M+H]^+$ Intermediate 4
8-Methoxy-2-methylquinoline-5-[N-(2-hydroxy-5-methoxyphenyl)]carboxamide A solution of 2-amino-4-methoxyphenol (3.8 g) in dry dimethylformamide (200 ml) was stirred at room temperature under nitrogen. Sodium hydride (3.9 g) was added and stirring continued for 2h. 8-Methoxy-2-methylquinoline-5-carbonyl chloride, hydrochloride (6.2 g; Intermediate 28 of PCT/GB97/01359) was added, and the resultant mixture was stirred overnight. The solvent was removed in vacuo and the residue purified by flash chromatography eluting with ethyl acetate to give the title compound as a brown solid (0.86 g).
TLC $R_f$ 0.30 (ethyl acetate)

Intermediate 5
2-(8-Methoxy-2-trifluoromethylquinolin-5-yl)-1H-benzimidazole-5-carboxylic acid, methyl ester 8-Methoxy-2-trifluoromethylquinoline-5-[N-(2-amino-5-carbomethoxyphenyl)]carboxamide (1.3 g) was suspended in phosphorus oxychloride (10 ml) and heated at reflux for 4h. The mixture was cooled to room temperature and concentrated in vacuo. The residue was neutralised by the addition of 46% aqueous sodium hydroxide solution and the resultant solid was collected by filtration and dried in vacuo. The title compound was obtained as a grey solid (1.3 g).
TLC $R_f$ 0.55 (ethyl acetate)

EXAMPLE 1
2-(8-Methoxyquinolin-5-yl)-1H-benzimidazole-5-carboxylic acid, methyl ester 8-Methoxyquinoline-5-[N-(2-amino-5-carbomethoxyphenyl)]carboxamide (919 mg) was suspended in phosphorus oxychloride (10 ml) and heated at reflux for 4h. The mixture was cooled to room temperature and concentrated in vacuo. The residue was basified to pH by the addition of saturated aqueous sodium hydrogen carbonate solution and the resultant solid was collected by filtration and dried in vacuo. The title compound was obtained as a light brown solid (850 mg).
NMR (400 MHz, d$_6$-DMSO) δ 9.79(d, 1H), 8.94(d, 1H), 8.38(d, 1H), 8.25(d, 1H), 7.88(d, 1H), 7.73(d, 1H), 7.70(d, 1H), 4.08(s, 3H), 3.89(s, 3H).

EXAMPLE 2
2-(8-Methoxyquinolin-5-yl)-1H-benzimidazole-5-carboxylic acid, methyl ester dihydrochloride A sample of 2-(8-methoxyquinolin-5-yl)-1H-benzimidazole-5-carboxylic acid, methyl ester (45 mg) was dissolved in 2M hydrochloric acid (3 ml), the resultant solution filtered and the filtrate concentrated in vacuo. The residue was triturated with dichloromethane and dried in vacuo to provide the title compound as a yellow solid (34 mg).
NMR (200 MHz, d$_6$-DMSO) δ 9.82(d, 1H), 9.10(d, 1H), 8.40(d, 1H), 8.32(bs, 1H), 7.90(bd, 2H), 7.87(d, 1H), 7.66(d, 1H), 4.18(s, 3H), 3.91(s, 3H).

EXAMPLE 3
2-(8-Methoxyquinolin-5-yl)-1H-benzimidazole-5-carboxylic acid dihydrochloride A mixture of 2-(8-methoxyquinolin-5-yl)-1H-benzimidazole-5-carboxylic acid, methyl ester (730 mg), 1M sodium hydroxide solution (40 ml) and ethanol (40 ml) was heated at reflux for 2h and then stirred at room temperature for 16h. The mixture was concentrated in vacuo and the residue acidified to pH 1 with concentrated hydrochloric acid and diluted with water (20 ml). The resultant solid was collected by filtration and then dissolved in methanol (30 ml). The solution was concentrated in vacuo and the resultant yellow solid dried over silica to provide the title compound (600 mg).
TLC R$_f$ 0.15 (1% acetic acid, 5% methanol in ethyl acetate) Mass spectrum (CI) 320 [M+H]$^+$

EXAMPLE 4
2-(8-Methoxy-2-methylquinone-5-yl)-5-methoxy-1H-benzimidazole

A solution of 4-methoxy-1,2-phenylenediamine (3.0 g) in dry pyridine (50 ml) and triethylamine (5.5 ml) was cooled to 0° C. under nitrogen. A suspension of 8-methoxy-2-methylquinoline-5-carbonyl chloride, hydrochloride (5.4 g; Intermediate 28 of PCT/GB97/01359) in dry tetrahydrofuran (60 ml) was added; the resultant suspension was allowed to warm to room temperature and then stirred overnight. The solvent was removed in vacuo and the residue partitioned between ethyl acetate (2×200 ml) and water (300 ml). The solid precipitate was removed by filtration and dried in vacuo at 50° C. to yield an off white solid (4.25 g). The crude amide (1.0 g) was suspended in phosphorus oxychloride (10 ml) and heated at reflux for 4h). The mixture was cooled to room temperature and concentrated in vacuo. The residue was diluted with water and left to stand for 2 days. The solution was basified to pH 14 by the addition of 46% aqueous sodium hydroxide solution and the resultant brown solid was collected by filtration and dried in vacuo to give a brown solid. Purification by flash chromatography eluting with 10% methanol/1% triethylamine/ethyl acetate followed by trituration with hexane gave the title compound as a beige solid (0.12 g).
TLC R$_f$ 0.32 (10% methanol in ethyl acetate) m.p. 145.5–147.5° C.

The following compounds were prepared in a similar manner using the appropriate starting materials.

EXAMPLE 5
2-(8-Methoxy-2-methoxyquinolin-5-yl)-5-aza-1H-benzimidazole

Prepared from 3,4-diaminopyridine, the title compound was obtained as a light brown solid (0.37 g).
TLC R$_f$ 0.54 (12% methanol in dichloromethane) m.p. 150° C. (dec.)

EXAMPLE 6
2-(8-Methoxy-2-methylquinolin-5-yl)-1-H-benzimidazole-5-carboxylic acid, methyl ester Prepared from methyl 3,4-diaminobenzoate; purification by flash chromatography eluting with ethyl acetate gave the title compound as a pale orange solid (0.17 g).
TLC R$_f$ 0.25 (ethyl acetate) m.p. 165–167° C.

EXAMPLE 7
2-(8-Methoxy-2-trifluoromethylquinolin-5-yl)-5-methoxy-1H-benzimidazole Prepared from 8-methoxy-2-trifluoromethylquinoline-5-carbonyl choride, hydrochloride (Intermediate 35 of PCT/GB97/01359) and 4-methoxy-1,2-phenylenediamine; purification by column chromatography eluting with 50%–70% ethyl acetate in hexane afforded the title compound as a pale yellow solid (1.32 g).
TLC R$_f$ 0.14 (50% ethyl acetate in hexane) m.p. 131–133° C.

EXAMPLE 8
2-(8-Methoxy-2-methylquinolin-5-yl)-5-methoxybenzoxazole

8-Methoxy-2-methylquinoline-5-[N-(2-hydroxy-5-methoxyphenyl)]carboxamide (0.86 g) was suspended in phosphorus oxychloride (8.8 ml) and heated at reflux for 5h. The mixture was cooled to room temperature and concentrated in vacuo. The residue was diluted with water and neutralised by the addition of 1N aqueous sodium hydroxide solution. The aqueous phase was extracted with dichloromethane (5×5 ml), dried (magnesium sulphate) and the solvent removed in vacuo to give a brown glass. Purification by flash chromatography eluting with ethyl acetate followed by trituration with acetone gave the title compound as a white solid (1.3 mg).
TLC R$_f$ 0.37 (ethyl acetate) NMR (200 Hz, CDCl$_3$) δ 2.9 (s, 3H), 3.9 (s, 3H), 4.2 (s, 3H), 7.0 (dd, 1H), 7.2 (d, 1H), 7.4 (d, 1H), 7.6 (dd, 2H), 8.4 (d, 1H), 9.9 (d, 1H).

EXAMPLE 9
(2-(8-Methoxy-2-trifluoromethylquinolin-5-yl)-5-methoxy-1-methyl-benzimidazole and 2-(8-Methoxy-2-trifluoromethylquinolin-5-yl)-6-methoxy-1-methyl-benzimidazole Sodium hydride (32 mg) was added to 2-[8-methoxy-2-trifluoromethylquinolin-5-yl)]-5-methoxy-1H-benzimidazole (0.25 g) in N,N-dimethylformamide (5 ml) at room temperature under an inert atmosphere. After stirring for 25 minutes iodomethane (0.06 ml) was added and the reaction stirred at room temperature overnight. The solvent was removed in vacuo and the residue partitioned between dichloromethane (2×45 ml) and water (45 ml). The combined organic phases were dried over magnesium sulphate and preadsorbed onto silica in vacuo. Purification by column chromatography eluting with 75% ethyl acetate in hexane afforded the title compound as a pale yellow solid (0.23 g) as a 1:1 mixture of the two isomers.

TLC R$_f$ 0.49 (75% ethyl acetate in hexane) Mass spectrum (Cl) 388 [M+H]$^+$

EXAMPLE 10
2-(8-Methoxy-2-trifluoromethylquinolin-5-yl)-1H-benzimidazole-5-carboxylic acid Sodium hydroxide (1M, 40 ml) was added to a stirred suspension of 2-(2-trifluoromethyl-8-methoxyquinolin-5-yl)-1H-benzimidazole-5-carboxylic acid, methyl ester (1 g) in ethanol (40 ml) at room temperature. The reaction was heated to 80° C. for 4h and cooled to room temperature. The ethanol was removed in vacuo and the remaining aqueous phase acidified to pH 5 with glacial acetic acid. The resulting solid was collected by filtration and dried in vacuo to give the titled compound as a brown solid (0.88 g).
m.p. 249° C. (dec.) Mass spectrum (CI) 388 [M+H]$^+$ The following compound was prepared in a similar manner using the appropriate starting materials.

EXAMPLE 11
2-(8-Methoxy-2-methylquinolin-5-yl)-1H-benzimidazole-5-carboxylic acid Prepared for 2-(8-Methoxy-2-methylquinolin-5-yl)-1H-benzimidazole-5-carboxylic acid, methyl ester, the title compound was obtained as a white solid (35 mg).
TLC R$_f$ 0.16 (10% methanol in dichloromethane) m.p. 205–207° C. (dec.)

EXAMPLE 12
2-(8-Methoxy-2-trifluoromethylquinolin-5-yl)-1H-benzimidazole-5-carboxamide Ammonia (0.5M in 1,4-dioxane, 3.9 ml) was added to a stirred solution of 2-(8-methoxy-2-trifluoromethylquinolin-5-yl)-1H-benzimidazole-5-carboxylic acid (0.15 g) in 1,4-dioxane (30 ml) at room temperature under an inert atmosphere. 1-(3-Dimethylaminopropyl)-3-ethylcarbodiimide hydrochloride (0.11 g) was added followed by 4-dimethylaminopyridine (36 mg) and the reaction stirred at room temperature overnight. The solvent was removed in vacuo and the residue partitioned between ethyl acetate (2×40 ml) and water (50 ml). The combined organic phases were dried over magnesium sulphate and preadsorbed onto silica in vacuo. Purification by column chromatography eluting with 10% methanol in ethyl acetate afforded the title compound as a cream solid (20 mg).
TLC R$_f$ 0.62 (10% methanol in ethyl acetate) m.p. 205–207° C.

EXAMPLE 13
8-Methoxy-2-methyl-5-phenylquinoline

5-Bromo-8-methoxy-2-methylquinoline (509 mg) and benzene boronic acid (323 mg) were added to a mixture of 2 M aqueous potassium carbonate (2 ml), toluene (10 ml) and ethanol (1 ml) and refluxed for 30 minutes under a nitrogen atmosphere. The mixture was cooled, triphenylphosphine (75 mg) and dichlorobis(triphenylphosphine) palladium chloride (66 mg) were added and the mixture was heated at 60° C. overnight. After cooling, the reaction mixture was diluted with ethyl acetate (30 ml). The organic phase was washed with 2 M aqueous potassium carbonate solution (2×30 ml), dried (magnesium sulphate), filtered and evaporated in vacuo to give the title compound (272 mg) as an off-white solid.
TLC R$_f$ 0.26 (dichloromethane) mp 133–134° C.
Assay methods The assays used to confirm the phosphodiesterase IV inhibitory activity of compounds of formula (i) are standard assay procedures as disclosed by Schilling et al, *Anal.* *Biochem.* 216:154 (1994), Thompson and Strada, *Adv. Cycl. Nucl. Res.* 8:119 (1979) and Gristwood and Owen, *Br. J. Pharmacol.* 87:91P (1986).

Compounds of formula (i) have exhibited activity at levels consistent with those believed to be useful in treating phosphodiesterase IV-related disease states in those assays.

The ability of compounds of formula (i) to inhibit TNF production in human peripheral blood mononuclear cells (PMBC's) is measured as follows. PMBC's are prepared from freshly taken blood or "Buffy coats" by standard procedures. Cells are plated out in RPMI1640+1% foetal calf serum in the presence and absence of inhibitors. LPS (100 ng/ml) is added and cultures are incubated for 22 h at 37° C. in an atmosphere of 95% air/5% $CO_2$. Supernatants are tested for TNFα by ELISA using commercially available kits.

In vivo activity in a skin eosinophilia model is determined by using the methods described by Hellewell et al, *Br. J. Pharmacol.* 111:811 (1994) and Br. J. Pharmacol. 110:416 (1993). Activity in a lung model is measured using the procedures described by Kallos and Kallos, *Int. Archs. Allergy Appl. Immunol.* 73:77 (1984), and Sanjar et al, *Br. J. Pharmacol.* 99:679 (1990).

An additional lung model, which allows measurement of inhibition of the early and late-phase asthmatic responses and also the inhibition of airway hyperactivity, is described by Broadley et al, *Pulmonary Pharmacol.* 7:311 (1994), J. Immunological Methods 190:51 (1996) and British J. Pharmacol. 116:2351 (1995).

Abbreviations
LPS Lipopolysaccharide (endotoxin)
ELISA Enzyme linked immunosorbent assay
What is claimed is:
1. A compound of the formula (i)

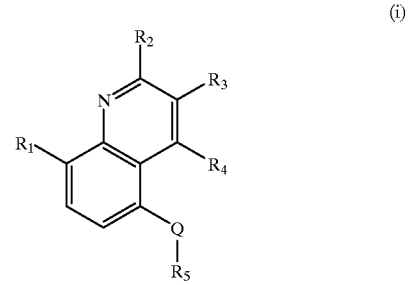

wherein
R$_1$ is selected from the group consisting of C$_{1-6}$ alkoxy (alkyl portion optionally substituted with one or more halogens), and thioalkyl;
R$_2$, R$_3$ and R$^4$, which may be the same or different, are each selected from the group consisting of OR$_{11}$, COR$_7$, CN, CO$_2$R$_8$, C(=NOR$_7$)R$_7$, alkyl-C(=NOR$_7$) R$_7$, halogen, CF$_3$, CONR$_{12}$R$_{13}$, NR$_9$R$_{10}$ and R$^7$;
R$_5$ represents H or a substituent selected from the group consisting of halogen, arylalkyl, heteroarylalkyl, heterocycloalkyl, alkyl, hydroxy, alkoxy, CO$_2$R$_8$, SO$_2$NR$_{12}$R$_{13}$, CONR$_{12}$R$_{13}$, —CN, NR$_9$R$_{10}$, COR$_{11}$, S(O)$_n$R$_{11}$ and tetrazolyl;
R$_7$ is selected from the group consisting of H, alkyl, cycloalkyl, aryl, heteroaryl, heterocyclo, arylalkyl, heteroarylalkyl and heterocycloalkyl, any of which may be optionally substituted at any position with R$_{16}$;
R$_8$ is selected from the group consisting of H, alkyl, arylalkyl, heteroarylalkyl and heterocycloalkyl;

$R_9$ is selected from the group consisting of alkylcarbonyl, alkoxycarbonyl, arylsulphonyl, heteroarylsulphonyl, heterocyclosulphonyl, arylcarbonyl, heteroarylcarbonyl, heterocyclocarbonyl and alkylsulphonyl and $R_{10}$ is selected from the group consisting of H and $R_{11}$, or $NR_9R_{10}$ represents a heterocyclic ring optionally substituted with one or more $R_{15}$;

$R_{11}$ is selected from the group consisting of alkyl, cycloalkyl, aryl, heteroaryl, heterocyclo, arylalkyl, heteroarylalkyl and heterocycloalkyl;

$R_{12}$ and $R_{13}$, which may be the same or different, each representing $R_7$, or $NR_{12}R_{13}$ represents a heterocyclic ring optionally substituted with one or more $R_{15}$;

$R_{15}$ is selected from the group consisting of alkyl, arylalkyl and heteroarylalkyl;

$R^{16}$ is selected from the group consisting of halogen, hydroxy, $OR_{11}$, $NR_9R_{10}$, CN, $CO_2H$, $CO_2R_{11}$, $CONR_{12}R_{13}$ and $COR_{11}$;

n represents 0–2; and

Q represents phenyl or pyridyl, optionally substituted at any position(s) with one or more substituents $R_5$;

or a pharmaceutically-acceptable salt thereof; and excluding 5-phenyl-8-mercaptoquinoline, 8-methoxy-5-phenylquinoline, 8-methoxy-5-[2-(t-butylcarbonylamino)phenyl]quinoline and 8-methoxy-5-[2-(t-butylcarbonylamino)-4-methoxyphenyl]quinoline).

2. The compound of claim 1, wherein $R_1$ is alkoxy optionally substituted with one or more halogens.

3. The compound of claim 1, wherein $R_2$ is H, alkyl, $CF_3$ or alkoxyalkyl.

4. The compound of claim 1, wherein one or both of $R_3$ and $R_4$ is H.

5. The compound of claim 1, wherein $R_5$ is H, $CO_2R_8$ or $CONR_{12}R_{13}$.

6. The compound of claim 1, which is 8-methoxy-2-methyl-5-phenylquinoline.

7. A pharmaceutical composition for therapeutic use comprising a compound of formula (i) as defined in claim 1 and a pharmaceutically-acceptable carrier or excipient.

8. A method for the treatment of a disease state capable of being modulated by inhibition of phosphodiesterase IV or Tumour Necrosis Factor, which comprises administering to a patient in need thereof an effective amount of a compound of the formula (i)

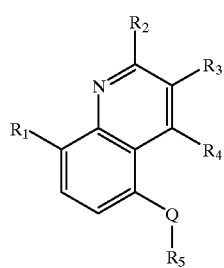

(i)

wherein:

$R_1$ is selected from the group consisting of $C_{1-6}$ alkoxy (alkyl portion optionally substituted with one or more halogens), and thioalkyl;

$R_2$, $R_3$ and $R_4$, which may be the same or different, are each selected from the group consisting of $OR_{11}$, $COR_7$, CN, $CO_2R_R$, $C(=NOR_7)R_7$, alkyl-$C(=NOR_7)$ $R_7$, halogen, $CF_3$, $CONR_{12}R_{13}$, $NR_9R_{10}$ and $R_7$;

$R^5$ represents H or a substituted selected from the group consisting of halogen, arylalkyl, heteroarylalkyl, heterocycloalkyl, alkyl, hydroxy, alkoxy, $CO_2R_8$, $SO_2NR_{12}R_{13}$, $CONR_{12}R_{13}$, —CN, $NR_9R_{10}$, $COR_{11}$ and $S(O)_{11}R_{11}$;

$R_7$ is selected from the group consisting of H, alkyl, cycloalkyl, aryl, heteroaryl, heterocyclo, arylalkyl, heteroarylalkyl and heterocycloalkyl, any of which may be optionally substituted at any position with $R_{16}$;

$R_8$ is selected from the group consisting of H, alkyl, arylalkyl, heteroarylalkyl and heterocycloalkyl;

$R_9$ is selected from the group consisting of alkylcarbonyl, alkoxycarbonyl, arylsulphonyl, heteroarylsulphonyl, heterocyclosulphonyl, arylcarbonyl, heteroarylcarbonyl, heterocyclocarbonyl and alkylsulphonyl and $R_{10}$ is selected from the group consisting of H and $R_{11}$, or $NR_9R_{10}$ represents a heterocyclic ring optionally substituted with one or more $R_{15}$;

$R_{11}$ is selected from the group consisting of alkyl, cycloalkyl, aryl, heteroaryl, heterocyclo, arylalkyl, heteroarylalkyl and heterocycloalkyl;

$R_{12}$ and $R_{13}$, which may be the same or different, each representing $R_7$, or $NR_{12}R_{13}$ represents a heterocyclic ring optionally substituted with one or more $R_{15}$;

$R_{15}$ is selected from the group consisting of alkyl, arylalkyl and heteroarylalkyl;

$R_{16}$ is selected from the group consisting of halogen, hydroxy, $OR_{11}$, $NR_9R_{10}$, CN, $CO_2H$, $CO_2R_{11}$, $CONR_{12}R_{13}$ and $COR_{11}$;

n represents 0–2; and

Q represents phenyl or pyridyl, optionally substituted at any position(s) with one or more substituents $R_5$;

or a pharmaceutically-acceptable salt thereof;

wherein said disease state is selected from the group consisting of an inflammatory disease, dementia, cardiac arrest, congestive heart failure and depression.

9. The method according to claim 8, wherein said inflammatory disease is asthma.

10. The method according to claim 8, wherein said dementia is selected from the group consisting of multi-infarct dementia and senile dementia.

11. A compound of the formula (ii)

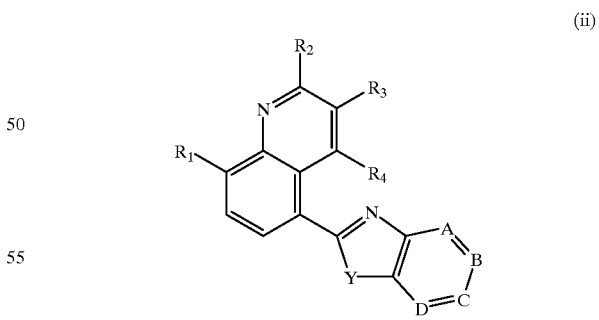

(ii)

wherein A, B, C and D are the same or different and are each N, CO or $CR_5$, provided that not more than two are N or NO;

Y represents $NR_{18}$, O or S;

$R_1$ is selected from the group consisting of $C_{1-6}$ alkoxy (alkyl portion optionally substituted with one or more halogens), and thioalkyl;

$R_2$, $R_3$ and $R_4$, which may be the same or different, are each selected from the group consisting of $OR_{11}$, $COR_7$, CN, $CO_2R_8$, $C(=NOR_7)R_7$, alkyl-$C(=NOR_7)R_7$, halogen, $CF_3$, $CONR_{12}R_{13}$, $NR_9R_{10}$ and $R_7$;

$R_5$ represents H or a substituent selected from the group consisting of halogen, arylalkyl, heteroarylalkyl, heterocycloalkyl, alkyl, hydroxy, alkoxy, $CO_2R_8$, $SO_9NR_{12}R_{13}$, $CONR_{12}R_{13}$, —CN, $NR_9R_{10}$, $COR_{11}$, $S(O)_nR_{11}$ and tetrazolyl;

$R_7$ is selected from the group consisting of H, alkyl, cycloalkyl, aryl, heteroaryl, heterocyclo, arylalkyl, heteroarylalkyl and heterocycloalkyl, any of which may be optionally substituted at any position with $R_{16}$;

$R_8$ is selected from the group consisting of H, alkyl, arylalkyl, heteroarylalkyl and heterocycloalkyl;

$R_9$ is selected from the group consisting of alkylcarbonyl, alkoxycarbonyl, arylsulphonyl, heteroarylsulphonyl, heterocyclosulphonyl, arylcarbonyl, heteroarylcarbonyl, heterocyclocarbonyl and alkylsulphonyl and $R_{10}$ is selected from the group consisting of H and $R_{11}$, or $NR_9R_{10}$ represents a heterocyclic ring optionally substituted with one or more $R_{15}$;

$R_{11}$ is selected from the group consisting of alyl, cycloalkyl, aryl, heteroaryl, heterocyclo, arylalkyl, heteroarylalkyl and heterocycloalkyl;

$R_{12}$ and $R_{13}$, which may be the same or different, each representing $R_7$, or $NR_{12}R_{13}$ represents a heterocyclic ring optionally substituted with one or more $R_{15}$;

$R_{15}$ is selected from the group consisting of alkyl, arylalkyl and heteroarylalkyl;

$R_{16}$ is selected from the group consisting of halogen, hydroxy, $OR_{11}$, $NR_9R_{10}$, CN, $CO_2H$, $CO_2R_{11}$, $CONR_{12}R_{13}$ and $COR_{11}$;

$R_{18}$ represents H or $C_{16}$ alkyl; and n represents 0–2;

or a pharmaceutically-acceptable salt thereof.

12. The compound of claim 11, wherein $R_2$, $R_3$ and $R_4$ are the same or different and are each $CF_3$, $COR_7$, $C(=NOH)R_7$, CN, $R_7$, alkyl, alkyl-$C(=NOR_7)R_7$ or alkyl-$C(=NOR)R_6$.

13. The compound of claim 11, wherein one of A, B, C and D is $CR_5$ and the others are CH;

$R_2$, $R_3$ and $R_4$ are the same or different and are each $R_7$, $COR_7$, $C(=NOR_7)R_7$, CN, $COOR_8$ or $CONR_{12}R_{13}$;

$R_5$ is $COOR_8$, $CONR_{12}R_{13}$, $NHSO_2CF_3$ or tetrazolyl; and $R_{12}$ and $R_{13}$ are each $R_7$.

14. The compound of claim 11, wherein $R_4$ is optionally-substituted alkoxy.

15. The compound of claim 11, which is 2-(8-methoxyquinolin-5-yl)-1H-benzimidazole-5-carboxylic acid as its methyl ester, dihydrochloride or methyl ester dihydrochloride.

16. The compound of claim 11, which is selected from the group consisting of 2-(8-methoxy-2-methylquinolin-5-yl)-5-methoxy-1H-benzimidazole, 2-(8-methoxy-2-trifluoromethylquinolin-5-yl)-5-methoxy-1H-benzimidazole, 2-(8-Methoxy-2-trifluoromethylquinolin-5-yl)-5-methoxy-1-methyl-benzimidazole, and 2-(8-Methoxy-2-trifluoromethyl-quinolin-5-yl)-6-methoxy-1-methyl-benzimidazole.

17. The compound of claim 11, which is selected from the group consisting of 2-(8-methoxy-2-methylquinolin-5-yl)-5-aza-1H-benzimidazole, 2-(8-methoxy-2-methylquinolin-5-yl)-1H-benzimidazole-5-carboxylic acid, methyl ester, 2-(8-methoxy-2-methylquinolin-5-yl)-5-methoxybenzoxazole, 2-(8-methoxy-2-trifluoromethylquinolin-5-yl)-1H-benzimidazoles-5-carboxylic acid, 2-(8-methoxy-2-methylquinolin-5-yl)-1H-benzimidazole-5-carboxylic acid, and 2-(8-methoxy-2-trifluoromethylquinolin-5-yl)-1H-benzimidazole-5-carboxamide.

18. A pharmaceutical composition for therapeutic use comprising a compound of formula (ii) as defined in claim 11 and a pharmaceutically-acceptable carrier or excipient.

19. A method for the treatment of a disease state capable of being modulated by inhibition of phosphodiesterase IV or Tumour Necrosis Factor, which comprises administering to a patient in need thereof an effective amount of a compound of claim 11, wherein said disease state is selected from the group consisting of an inflammatory disease, dementia, cardiac arrest, congestive heart failure and depression.

20. The method according to claim 19, wherein said inflammatory disease is asthma.

21. The method according to claim 19, wherein said dementia is selected from the group consisting of multi-infarct dementia and senile dementia.

* * * * *

UNITED STATES PATENT AND TRADEMARK OFFICE
CERTIFICATE OF CORRECTION

PATENT NO.   : 6,069,151
DATED        : May 30, 2000
INVENTOR(S)  : Hazel Joan Dyke, John Gary Montana, Alan Findley Haughan, Verity M. Sabin It is certified that error appears in the above-identified patent and that said Letters Patent is hereby corrected as shown below:

Column 14,
Line 56, "and $R^7$" should read -- and $R_7$ --.

Column 15,
Line 66, "$CO_2R_R$" should read -- $CO_2R_8$ --.

Column 16,
Line 1, "substituted" should read -- substituent --.
Line 5, "$S(O)_{11}R_{11}$" should read -- $S(O)_nR_{11}$ --.
Line 61, "N, CO" should read -- N, NO --.

Column 17,
Line 6, "$SO_9NR_{12}R_{13}$," should read -- $SO_2NR_{12}R_{13}$, --.
Line 21, "alyl" should read -- alkyl --.
Line 34, "C16" should read -- $C_{1-6}$ --.
Lines 30-40, "or alkyl-C(—NOR)$R_6$" should read -- or alkyl-C(=NOR)$R_6$ --.

Column 18,
Line 27, "benzimidazoles" should read -- benzimidazole --.

Signed and Sealed this

Fifth Day of March, 2002

Attest:

JAMES E. ROGAN
Attesting Officer         Director of the United States Patent and Trademark Office